United States Patent
Park et al.

(10) Patent No.: US 9,000,071 B2
(45) Date of Patent: Apr. 7, 2015

(54) EPOXY RESIN, EPOXY RESIN COMPOUND COMPRISING THE SAME, AND RADIANT HEAT CIRCUIT BOARD USING THE COMPOUND

(71) Applicant: LG Innotek Co., Ltd., Seoul (KR)

(72) Inventors: Jae Man Park, Seoul (KR); Hae Yeon Kim, Seoul (KR); SungBae Moon, Seoul (KR); Jeungook Park, Seoul (KR); SungJin Yun, Seoul (KR); JongHeum Yoon, Seoul (KR); Hyuk Soo Lee, Seoul (KR); Jaehun Jeong, Seoul (KR); In Hee Cho, Seoul (KR)

(73) Assignee: LG Innotek Co., Ltd., Seoul (KR)

(*) Notice: Subject to any disclaimer, the term of this patent is extended or adjusted under 35 U.S.C. 154(b) by 0 days.

(21) Appl. No.: 13/872,682

(22) Filed: Apr. 29, 2013

(65) Prior Publication Data
US 2013/0284502 A1  Oct. 31, 2013

(30) Foreign Application Priority Data
Apr. 30, 2012 (KR) .................. 10-2012-0045842

(51) Int. Cl.
*C08L 63/00* (2006.01)
*C07D 303/46* (2006.01)
*H05K 1/05* (2006.01)
*C08G 59/28* (2006.01)

(52) U.S. Cl.
CPC ............ *C08L 63/00* (2013.01); *C07D 303/46* (2013.01); *H05K 1/05* (2013.01); *C08G 59/28* (2013.01)

(58) Field of Classification Search
CPC ...................................... C07D 303/46
See application file for complete search history.

(56) References Cited

U.S. PATENT DOCUMENTS

| 5,364,912 | A  | * | 11/1994 | Hefner et al. ................. 525/418 |
| 2004/0224163 | A1 | * | 11/2004 | Tobita et al. .................. 428/413 |
| 2007/0116938 | A1 | * | 5/2007 | Tobita et al. ............... 428/292.1 |
| 2007/0184280 | A1 | * | 8/2007 | Tanaka et al. ................. 428/413 |

FOREIGN PATENT DOCUMENTS

| EP | 1481999 A2 | 12/2004 |
| WO | WO-2013/009114 A2 | 1/2013 |

OTHER PUBLICATIONS

European Search Report dated Feb. 4, 2015 in European Application No. 13165059.0.

* cited by examiner

*Primary Examiner* — Mark Kaucher
*Assistant Examiner* — Kregg Brooks
(74) *Attorney, Agent, or Firm* — Saliwanchik, Lloyd & Eisenschenk

(57) ABSTRACT

An epoxy resin compound including an epoxy resin, a hardening agent, and an inorganic filler as a main component is provided. The epoxy resin includes an epoxy resin represented by a chemical formula. Therefore, the epoxy resin having a mesogen structure that increases crystallinity is used, and thus thermal conductivity can be increased. Further, the epoxy resin is used as an insulating material for a printed circuit board, and thus a high radiant heat substrate can be provided.

16 Claims, 1 Drawing Sheet

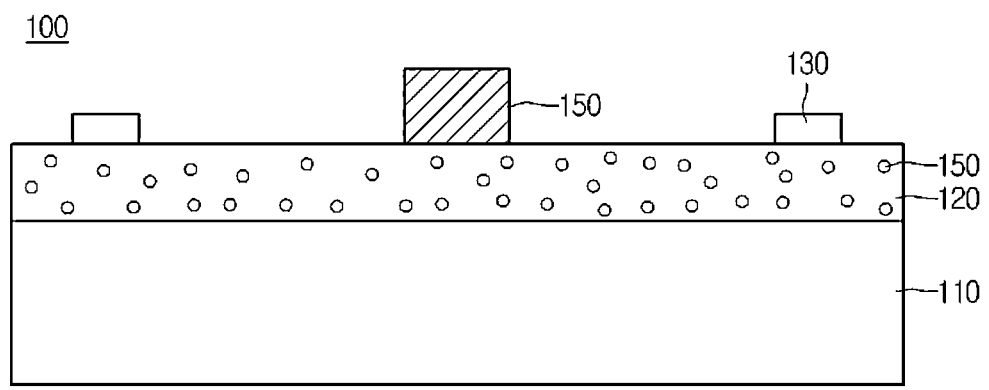

EPOXY RESIN, EPOXY RESIN COMPOUND COMPRISING THE SAME, AND RADIANT HEAT CIRCUIT BOARD USING THE COMPOUND

CROSS-REFERENCE TO RELATED APPLICATION

This application claims the benefit under 35 U.S.C. §119 of Korean Patent Application No. 10-2012-0045842, filed Apr. 30, 2012, which is hereby incorporated by reference in its entirety.

BACKGROUND

1. Field of the Invention

The present invention relates to an epoxy resin, and more particularly, to an epoxy resin, an epoxy resin compound comprising the same, and a radiant heat circuit board using the epoxy resin compound as an insulating layer.

2. Discussion of Related Art

A circuit board includes a circuit pattern formed on an insulating layer, and thus various electronic devices can be mounted on the circuit board.

One of the electronic devices mounted on the circuit board may be, for example, a heating element. Heat radiated from the heating element may cause performance deterioration of the circuit board. With a recent trend of high integration and high capacity of electronic devices, interest in heat radiation in a circuit board has been increasing.

In order to obtain an insulating layer having both electrical insulation and high thermal conductivity, an epoxy resin compound including a bisphenol A-type or bisphenol F-type epoxy resin has been used.

However, the epoxy resin compound cannot satisfy required thermal conductivity. Further, the bisphenol A-type or bisphenol F-type epoxy resin does not have suitable hardening, mechanical strength, and toughness due to its low viscosity. Since a bisphenol A-type or bisphenol F-type epoxy resin stays in a liquid form at room temperature, it is difficult to treat.

BRIEF SUMMARY

The present invention is directed to providing an epoxy resin having high crystallinity, an epoxy resin compound including the epoxy resin, and a radiant heat circuit board using the epoxy resin compound.

An epoxy resin in accordance with an exemplary embodiment is represented by the following Chemical Formula 1:

wherein n is from 1 to 3, m is from 1 to 3, $R^1$ represents one to three aryl groups, $R^2$ represents one to three aryl groups, and $R^3$, $R^4$, $R^5$, $R^6$, $R^7$ and $R^8$ are independently selected from the group consisting of hydrogen, an alkyl group having 1 to 30 carbon atoms, a halogen, an aryl group, an alkoxy group, an amino group, a hetero aryl group and a carboxylic group.

An epoxy resin compound in accordance with an exemplary embodiment of the present invention includes an epoxy resin, a hardening agent, and an inorganic filler, in which the epoxy resin includes the epoxy resin represented by Chemical Formula 1.

A radiant heat circuit board in accordance with an exemplary embodiment of the present invention includes a metal plate, an insulating layer formed on the metal plate, and a circuit pattern formed on the insulating layer, wherein the insulating layer is formed by hardening the epoxy resin compound.

BRIEF DESCRIPTION OF THE DRAWING

The above and other objects, features and advantages of the present invention will become more apparent to those of ordinary skill in the art by describing in detail exemplary embodiments thereof with reference to the attached drawings, in which:

FIG. 1 is a cross-sectional view of a radiant heat circuit board in accordance with an exemplary embodiment of the present invention.

DETAILED DESCRIPTION

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

It will be understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

In drawings, parts irrelevant to the description are omitted for simplicity of explanation, various layers and regions are illustrated as being thick in an exaggerated form for clarity of illustration, and like reference numerals denote like parts through the whole document.

[Chemical Formula 1]

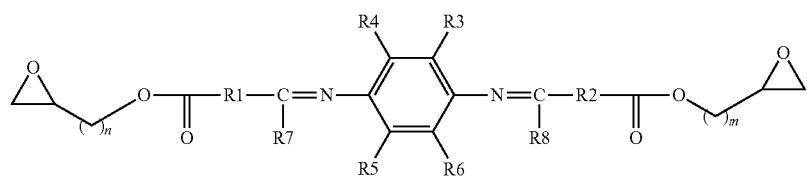

It will be further understood that when an element such as a layer, a film, a region, a plate, and the like is referred to as being "on" or "above" another element, it can be directly on or directly above the other element or intervening elements may be present. In contrast, when an element is referred to as being "directly on" or "directly above" another element, there are no intervening elements present.

With reference to the appended drawings, exemplary embodiments of the present invention will be described in detail below. To aid in understanding the present invention, like numbers refer to like elements throughout the description of the figures, and the description of the same elements will be not reiterated.

Herein, wt % can be substituted with parts by weight.

In accordance with an exemplary embodiment of the present invention, there is provided an epoxy resin compound having high crystallinity and high thermal conductivity.

The epoxy resin compound in accordance with an exemplary embodiment of the present invention includes an epoxy resin including a mesogen structure, a hardening agent, and an inorganic filler. Herein, a mesogen is a fundamental unit of a liquid crystal and includes a rigid structure. The mesogen may include a rigid structure such as biphenyl.

The epoxy resin compound in accordance with an exemplary embodiment of the present invention may include an epoxy resin of 3 to 60 wt % with respect to the whole epoxy resin compound. If the epoxy resin is included at 3 wt % or more with respect to the whole epoxy resin compound, adhesivity may be improved. If the epoxy resin is included at 60 wt % or less with respect to the whole epoxy resin compound, a thickness may be adjusted easily.

In this case, the epoxy resin compound may include a crystalline epoxy resin of 12 wt % or more with respect to the whole epoxy resin. If the crystalline epoxy resin is 12 wt % or more with respect to the whole epoxy resin, the epoxy resin compound may be crystallized easily and may have high thermal conductivity.

Herein, the crystalline epoxy resin may be a compound represented by the following Chemical Formula 1:

wherein n is from 1 to 3, m is from 1 to 3, $R^1$ represents one to three aryl groups, $R^2$ represents one to three aryl groups, and $R^3$, $R^4$, $R^5$, $R^6$, $R^7$ and $R^8$ may be independently selected from the group consisting of hydrogen, an alkyl group having 1 to 30 carbon atoms, a halogen, an aryl group, an alkoxy group, an amino group, a hetero aryl group, and a carboxylic group.

To be more specific, the alkyl group may be selected from a methyl group or an ethyl group. The halogen may be selected from fluorine or chlorine. The aryl group may be selected from benzene or naphthalene.

To be more specific, n may be 1 and m may be 1. Further, $R^1$ and $R^2$ may represent one aryl group. Furthermore, $R^3$, $R^4$, $R^5$, $R^6$, $R^7$, $R^8$, $R^9$, $R^{10}$, and $R^{11}$ selected may be independently from hydrogen or a methyl group. To be more specific, $R^7$ and $R^8$ may be hydrogen and $R^3$, $R^4$, $R^5$, and $R^6$ may be independently selected from hydrogen or a methyl group.

The crystalline epoxy resin may also be represented by the following Chemical Formula 2:

[Chemical Formula 2]

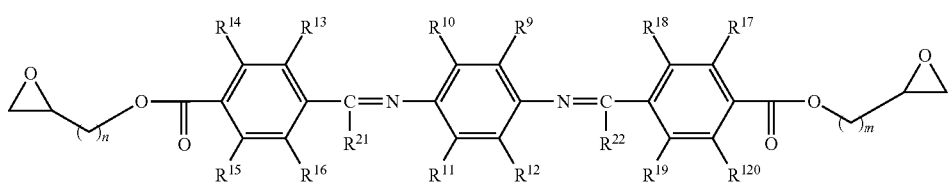

wherein n is from 1 to 3, m is from 1 to 3, and $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ may be independently selected from the group consisting of hydrogen, an alkyl group having 1 to 30 carbon atoms, a halogen, an aryl group, an alkoxy group, an amino group, a hetero aryl group, and a carboxylic group.

To be more specific, the alkyl group may be selected from a methyl group or an ethyl group. The halogen may be selected from fluorine or chlorine. The aryl group may be selected from benzene or naphthalene.

To be more specific, n may be 1 and m may be 1. Further, $R^9$ to $R^{22}$ may be independently selected from hydrogen or a methyl group. To be more specific, $R^{21}$ and $R^{22}$ may be hydrogen and $R^9$ to $R^{20}$ may be independently selected from hydrogen or a methyl group.

If $R^9$ to $R^{22}$ are hydrogen, the crystalline epoxy resin may also be represented by the following Chemical Formula 3:

[Chemical Formula 1]

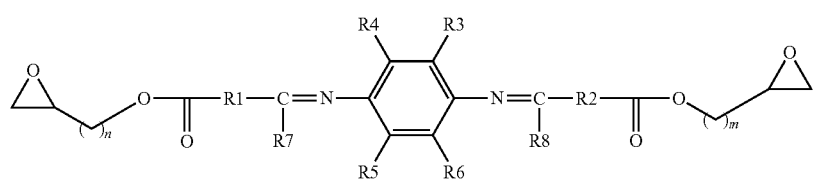

[Chemical Formula 3]

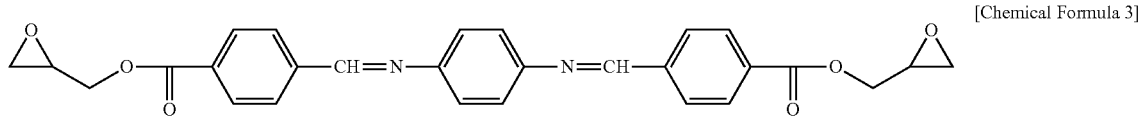 [SMILES: O=C(OCC1CO1)c1ccc(C=Nc2ccc(N=Cc3ccc(C(=O)OCC4CO4)cc3)cc2)cc1]

The crystalline epoxy resin (hereinafter referred to as "bis(oxiran-2-ylmethyl)4,4'-(1,4-phenylenebis(azan-1-yl-1-ylidene))bis(methan-1-yl-1-ylidene)dibenzoate") represented by Chemical Formula 3 has a melting point of 158° C. and H-NMR values (nuclear magnetic resonance values of hydrogen) of δ=8.58 (s, 2H), δ=8.17-8.19 (d, 4H), δ=7.99-8.01 (d, 4H), =7.33 (s, 4H), δ=4.69-4.72 (d, 1H), δ=4.18-4.22 (m, 1H), δ=3.36-3.40 (m, 1H), δ=2.92-2.94 (m, 1H), and δ=2.74-2.77 (m, 1H). The melting point is measured at a heating rate of 10° C./min using a differential scanning calorimeter (DSC Q100 manufactured by TA Instruments). For NMR, the H-NMR values are measured after dissolution in $CDCL_3$-d6.

The crystalline epoxy resin represented by Chemical Formula 3 may be synthesized by the following mechanism.

maintained for 24 hours. When a yellow solid is precipitated, it is filtered and purified with methanol several times and dried in a vacuum at 40° C.

After the first step, an intermediate (AE2-1) may be obtained at a yield of 91% or more.

Then, in the second step, 5 g of the intermediate synthesized in the first step and 50 ml of DMAc are added, heated and stirred, and then 52.7 ml of epichlorohydrin and 0.22 g of TBAB as a catalyst are added thereto at room temperature. The resulting mixture is heated to 110° C. and stirred for 6 hours.

The reaction mixture is slowly cooled to room temperature and poured into methanol. If a yellow solid remains after filtering, it is washed several times with methanol and dried in a vacuum at 40° C.

First step

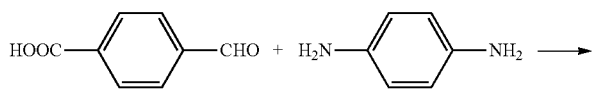

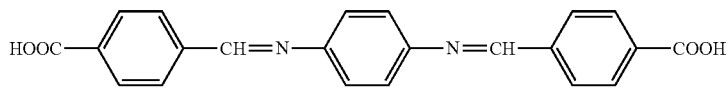

Second step

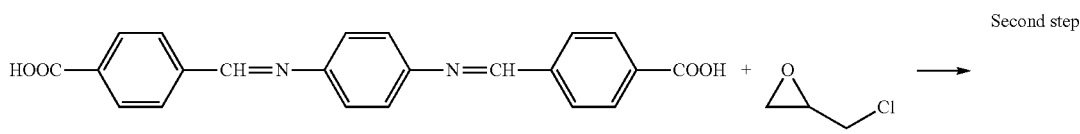

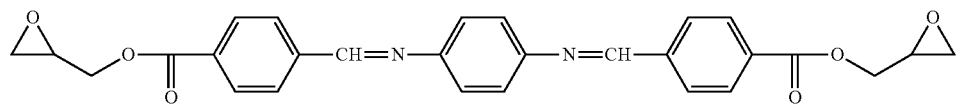

In other words, in the first step, 3 g of 4-carboxybenzaldehyde is dissolved in methanol, and 1.08 g of p-phenylenediamine is added dropwise thereto with strong stirring and then After the second step, the epoxy compound represented by Chemical Formula 3 may be obtained at a yield of 65% or more.

In an exemplary embodiment of the present invention, the crystalline epoxy resin may also be represented by the following Chemical Formula 4:

[Chemical Formula 4]

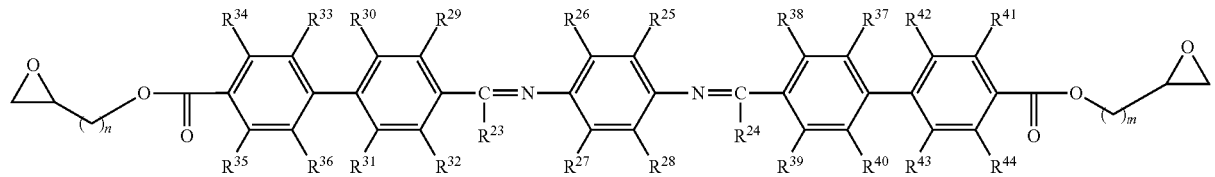

wherein n is from 1 to 3, m is from 1 to 3, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, and $R^{44}$ may be independently selected from the group consisting of hydrogen, an alkyl group having 1 to 30 carbon atoms, a halogen, an aryl group, an alkoxy group, an amino group, a hetero aryl group, and a carboxylic group.

To be more specific, the alkyl group may be selected from a methyl group or an ethyl group. The halogen may be selected from fluorine or chlorine. The aryl group may be selected from benzene or naphthalene.

To be more specific, n may be 1 and m may be 1. Further, $R^{23}$ to $R^{44}$ may be independently selected from hydrogen or a methyl group. To be more specific, $R^{23}$ and $R^{24}$ may be hydrogen and $R^{25}$ to $R^{44}$ may be independently selected from hydrogen or a methyl group.

Meanwhile, the epoxy resin represented by one of Chemical Formula 1 to Chemical Formula 4 has high crystallinity, and thus thermal conductivity may be high but room temperature stability may be low. In order to solve this problem, the epoxy resin compound in accordance with an exemplary embodiment of the present invention may further include another typical non-crystalline epoxy resin having two or more epoxy groups in molecules in addition to the crystalline epoxy resin represented by one of Chemical Formula 1 to Chemical Formula 4.

Examples of the non-crystalline epoxy resin may include a glycidyl etheride induced from one of bisphenol A, bisphenol F, 3,3',5,5'-tetramethyl-4,4'-dihydroxydiphenylmethane, 4,4'-dihydroxydiphenylsulfone, 4,4'-dihydroxydiphenylsulfide, 4,4'-dihydroxydiphenylketone, fluorenbisphenol, 4,4'-biphenol,3,3',5,5'-tetramethyl-4,4'-dihydroxybiphenyl, 2,2'-biphenol, resorcin, catechol, t-butylcatechol, hydroquinone, t-butylhydroquinone, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,4-dihydroxynaphthalene, 2,5-dihydroxynaphthalene, 2,6-dihydroxynaphthalene, 2,7-dihydroxynaphthalene, 2,8-dihydroxynaphthalene, allylide or polyallylide of the above-described dihydroxynaphthalene, divalent phenols such as allylated bisphenol A, allylated bisphenol F, and allylated phenolnovolac, or phenolnovolac, bisphenol A novolac, o-cresolnovolac, m-cresolnovolac, p-cresolnovolac, xylenolnovolac, poly-p-hydroxystyrene, tris-(4-hydroxyphenyl)methane, 1,1,2,2-tetrakis(4-hydroxyphenyl)ethane, fluoroglycinol, pyrogallol, t-butylpyrogallol, allylated pyrogallol, polyallylated pyrogallol, 1,2,4-benzenetriol, 2,3,4-trihydroxybenzophenone, phenols of trivalence or more such as a phenolaralkyl resin, a naphtolaralkyl resin, a dicyclopentadiene-based resin, and halogenated bisphenols such as tetrabromobisphenol A, and combinations selected therefrom.

The epoxy resin compound in accordance with an exemplary embodiment of the present invention may include a hardening agent of 0.5 wt % to 5 wt % with respect to the whole epoxy resin compound. If the hardening agent is included at 0.5 wt % or more with respect to the whole epoxy resin compound, adhesivity may be improved. In addition, if the hardening agent is included at 5 wt % or less with respect to the whole epoxy resin compound, a thickness may be adjusted easily. As the hardening agent, all kinds of epoxy resin hardening agents generally known may be used, and desirably, a phenol-based hardening agent may be used.

The phenol-based hardening agent is a single compound among phenolic compounds and includes a phenol resin as well as a phenol compound.

Specific examples of the phenol-based hardening agent may include bisphenol A, bisphenol F, 4,4'-dihydroxydiphenylmethane, 4,4'-dihydroxydiphenylether, 1,4-bis(4-hydroxyphenoxy)benzene, 1,3-bis(4-hydroxyphenoxy)benzene, 4,4'-dihydroxydiphenylsulfide, 4,4'-dihydroxydiphenylketone, 4,4'-dihydroxydiphenylsulfone, 4,4'-dihydroxybiphenyl, 2,2'-dihydroxybiphenyl, 10-(2,5-dihydroxyphenyl)-10H-9-oxa-10-phosphaphenanthrene-10-oxide, phenolnovolac, bisphenol A novolac, o-cresolnovolac, m-cresolnovolac, p-cresolnovolac, xylenolnovolac, poly-p-hydroxystyrene, hydroquinone, resorcin, catechol, t-butylcatechol, t-butylhydroquinone, fluoroglycinol, pyrogallol, t-butylpyrogallol, allylated pyrogallol, polyallylated pyrogallol, 1,2,4-benzenetriol, 2,3,4-trihydroxybenzophenone, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,4-dihydroxynaphthalene, 2,5-dihydroxynaphthalene, 2,6-dihydroxynaphthalene, 2,7-dihydroxynaphthalene, 2,8-dihydroxynaphthalene, allylide or polyallylide of the above-described dihydroxynaphthalene, allylated bisphenol A, allylated bisphenol F, allylated phenolnovolac, and allylated pyrogallol.

Two or more kinds of hardening agents may be mixed and used as the hardening agent.

Meanwhile, instead of the phenol-based hardening agent, a generally-known hardening agent may be used. Examples of the generally-known hardening agent may include an amine-based hardening agent, an acid anhydride-based hardening agent, a polymercaptan-based hardening agent, a polyaminoamide-based hardening agent, an isocyanate-based hardening agent, a blocked isocyanate-based hardening agent, and the like. A mixture ratio of these hardening agents may be appropriately determined in the light of kinds of hardening agents to be mixed or physical properties of a thermal conductive epoxy resin molding to be obtained.

Specific examples of the amine-based hardening agent may include aliphatic amines, polyether polyamines, alicyclic amines, and aromatic amines. The aliphatic amines may include ethylenediamine, 1,3-diaminopropane, 1,4-diaminopropane, hexamethylenediamine, 2,5-dimethylhexamethylenediamine, trimethylhexamethylenediamine, diethylenetriamine, iminobis(propylamine), bis(hexamethylene)triamine, triethylenetetramine, tetraethylenepentamine, pentaethylenehexamine, N-hydroxyethylethylenediamine, and tetra(hydroxyethyl)ethylenediamine. The polyether polyamines may include triethyleneglycoldiamine, tetraethylenglycoldiamine, diethyleneglycolbis(propylamine), polyoxypropylenediamine, and polyoxypropylenetriamines. The alicyclic amines may include isophoronediamine, methanediamine, N-aminoethylpiperazine, bis(4-amino-3-methyldicyclohexyl)methane, bis(aminomethyl)cyclohexane, 3,9-bis(3-aminopropyl)2,4,8,10-tetraoxaspiro(5,5)undecane, and norbornenediamine. The aromatic amines may include tetrachloro-p-xylenediamine, m-xylenediamine, p-xylenediamine, m-phenylenediamine, o-phenylenediamine, p-phenylenediamine, 2,4-diaminoanisole, 2,4-toluenediamine, 2,4-diaminodiphenylmethane, 4,4'-diaminodiphenylmethane, 4,4'-diamino-1,2-diphenylethane, 2,4-diaminodiphenylsulfone, 4,4'-diaminodiphenylsulfone, m-aminophenol, m-aminobenzylamine, benzyldimethylamine, 2-(dimethylaminomethyl)phenol, triethanolamine, methylbenzylamine, α-(m-aminophenyl)ethylamine, α-(p-aminophenyl)ethylamine, diaminodiethyldimethyldiphenylmethane, and α,α'-bis(4-aminophenyl)-p-disopropylbenzene.

Specific examples of the acid anhydride-based hardening agent may include dodecenyl succinic anhydride, poly(adipic anhydride), poly(azelaic anhydride), poly(sebacic anhydride), poly(ethyloctadecanedioic)anhydride, poly(phenylhexadecanedioic)anhydride, methyl tetra-hydrophthalic anhydride, methyl hexa-hydrophthalic anhydride, hexa-hydrophthalic anhydride, methyl himic anhydride, tetra-hydrophthalic anhydride, trialkyl tetra-hydrophthalic anhydride, methylcyclohexane dicarboxylic anhydride, methylcyclohexene tetracarboxylic anhydride, phthalic anhydride, trimellitic anhydride, pyromellitic anhydride, benzophenon tetracarboxylic anhydride, ethylene glycol bistri-mellitate anhydride, Het anhydride, nadic anhydride, methyl nadic anhydride, 5-(2,5-dioxotetrahydro-3-furanyl)-3-methyl-3-cyclohexane-1,2-dicarboxylic anhydride, 3,4-dicarboxy-1,2,3,4-tetrahydro-1-naphthalenesuccinic dianhydride, and 1-methyl-dicarboxy-1,2,3,4-tetrahydro-1-naphthalenesuccinic dianhydride.

The epoxy resin compound in accordance with an exemplary embodiment of the present invention includes an inorganic filler of 40 wt % to 97 wt % with respect to the whole epoxy resin compound.

If the inorganic filler is included at 40 wt % or more with respect to the whole epoxy resin compound, high thermal conductivity, low thermal expansibility, and high heat resistance may be guaranteed. The effects may be increased as the amount of the inorganic filler added is increased. However, the effect is not increased in proportion to a volume ratio of the inorganic filler but rapidly increased from a certain amount of the inorganic filler added. The physical properties may be obtained by controlling a higher-order structure in a polymer state. The higher-order structure is mainly formed on a surface of the inorganic filler, and thus, a specific amount of the inorganic filler is needed. However, if the inorganic filler is included in 97 wt % or more with respect to the whole epoxy resin compound, viscosity may be increased, and thus, moldability may be deteriorated.

The inorganic filler may have a round shape. The inorganic filler is not specifically limited as long as it has a round shape, and may include inorganic filler having an elliptic cross section. However, it is preferable that the inorganic filler may have a perfectly round shape in view of improvement in fluidity.

The inorganic filler may include alumina, aluminum nitride, silicon nitride, boron nitride or crystalline silica, and two or more different kinds of inorganic fillers may be mixed and used.

The inorganic filler may have an average particle diameter of 30 μm or less. If an average particle diameter is greater than 30 μm, fluidity of the epoxy resin compound may be deteriorated and strength thereof may also be deteriorated.

The epoxy resin compound in accordance with an exemplary embodiment of the present invention may further include a known hardening accelerator. Examples of the hardening accelerator may include amines, imidazols, organic phosphines, and lewis acid. To be specific, the hardening accelerator may include tertiary amines such as 1,8-diazabicyclo(5,4,0)undesen-7, triethylenediamine, benzyldimethylamine, triethanolamine, dimethylaminoethanol, and tris(dimethylaminomethyl)phenol, imidazols such as 2-methylimidazole, 2-phenylimidazole, 2-phenyl-4-methylimidazole, and 2-heptadecylimidazole, organic phosphines such as tributylphosphine, methyldiphenylphosphine, triphenylphosphine, diphenylphospine, and phenylphosphine, tetra-substituted phosphonium tetra-substituted borate such as tetraphenyl phosphonium tetraphenyl borate, tetraphenyl phosphonium ethyltriphenyl borate, and tetrabutyl phosphonium tetrabutyl borate, and tetraphenyl boron salt such as 2-ethyl-4-methylimidazole tetraphenyl borate and N-methylmorpholine tetraphenyl borate.

The epoxy resin compound in accordance with an exemplary embodiment of the present invention may further include a release agent. Typically, wax is used as a release agent for an epoxy resin compound and may include, for example, stearic acid, montanic acid, montanic acid ester, and phosphoric acid ester.

The epoxy resin compound in accordance with an exemplary embodiment of the present invention may further include a coupling agent in order to improve adhesivity between an inorganic filler and a resin. By way of example, epoxysilane may be used as the coupling agent.

In order to obtain the epoxy resin compound in accordance with an exemplary embodiment of the present invention, the epoxy resin, the hardening agent, and other components besides the coupling agent are dissolved in a solvent such as acetone, MEK, MIBK, IPA, butanol or toluene, and heated and stirred. The inorganic filler is added thereto, and then the resulting mixture is uniformly mixed by a mixer. Then, the coupling agent is added thereto, and the resulting mixture is mixed and kneaded by a heating roll and a kneader. There is no specific limitation on an order of mixing the components.

In this case, the solvent may occupy 10 wt % to 20 wt % with respect to the total weight of the epoxy resin compound.

The epoxy resin compound in accordance with an exemplary embodiment of the present invention can be applied to a radiant heat circuit board as illustrated in FIG. 1.

Referring to FIG. 1, a radiant heat circuit board 100 includes a metal plate 110, an insulating layer 120 formed on the metal plate 110, and circuit patterns 130 formed on the insulating layer 120.

The metal plate 110 may be made of one of alloys containing copper, aluminum, nickel, gold or platinum having high thermal conductivity.

The metal plate 110 may include a metal protrusion (not illustrated) constituting a mounting pad for mounting a heating element 150.

The metal protrusion is extended from the metal plate 110 and protruded vertically. An upper surface of the metal protrusion may partially serve as a mounting pad for mounting the heating element 150 and have a predetermined width such that solder may be positioned thereon.

The insulating layer 120 is formed on the metal plate 110.

The insulating layer 120 may be formed of a plurality of insulating layers and insulates the circuit patterns 130 disposed on the insulating layer 120 from the metal plate 110.

The insulating layer 120 may be formed by hardening the epoxy resin compound in accordance with the exemplary embodiment of the present invention. Within the insulating layer 120, an inorganic filler 125 is uniformly dispersed.

The plurality of circuit patterns 130 may be formed on the insulting layer 120.

Since the insulating layer 120 is formed using the epoxy resin compound in accordance with the exemplary embodiment of the present invention, thermal conductivity is improved, and thus heat radiated from the heating element 150 can be transferred to the metal plate 110.

Hereinafter, the present invention will be described in more detail with reference to Examples and Comparative Examples.

EXAMPLES

Example 1

12.5 wt % of bisphenol A type epoxy resin, 2.2 wt % of o-cresol-novolac epoxy resin, 1.7 wt % of a crystalline epoxy resin represented by Chemical Formula 3, 5 wt % of epoxy resin NC-3000, 2 wt % of a biphenol hardening agent, 0.2 wt % of 2-methyl imidazole hardening accelerator, and 1 wt % of BYK-W980 additive were all mixed together and stirred at 40° C. for 10 minutes. Then, 75.4 wt % of an alumina inorganic filler was added thereto, and then the resulting mixture was stirred at room temperature for 20 minutes to 30 minutes. As a result, an epoxy resin compound of Example 1 was obtained.

Example 2

4.2 wt % of o-cresol-novolac epoxy resin, 2.5 wt % of a crystalline epoxy resin represented by Chemical Formula 3, 8.5 wt % of an epoxy resin NC-3000, 2.2 wt % of a biphenol hardening agent, 0.1 wt % of 2-methyl imidazole hardening accelerator, and 0.5 wt % of BYK-W980 additive were all mixed together and stirred at 40° C. for 10 minutes. Then, 82 wt % of an alumina inorganic filler was added thereto, and then the resulting mixture was stirred at room temperature for 20 minutes to 30 minutes. As a result, an epoxy resin compound of Example 2 was obtained.

Example 3

2 wt % of bisphenol A type epoxy resin, 8 wt % of a crystalline epoxy resin represented by Chemical Formula 3, 4.5 wt % of epoxy resin NC-3000, 1.3 wt % of a biphenol hardening agent, 0.2 wt % of 2-methyl imidazole hardening accelerator, and 1 wt % of BYK-W980 additive were all mixed together and then stirred at 40° C. for 10 minutes. Then, 83 wt % of an alumina inorganic filler was added thereto, and then the resulting mixture was stirred at room temperature for 20 minutes to 30 minutes. As a result, an epoxy resin compound of Example 3 was obtained.

Example 4

3 wt % of bisphenol A type epoxy resin, 12 wt % of a crystalline epoxy resin represented by Chemical Formula 3, 3 wt % of epoxy resin NC-3000, 1.1 wt % of a biphenol hardening agent, 0.1 wt % of 2-methyl imidazole hardening accelerator, and 0.8 wt % of BYK-W980 additive were all mixed together and then stirred at 40° C. for 10 minutes. Then, 80 wt % of an alumina inorganic filler was added thereto, and then the resulting mixture was stirred at room temperature for 20 minutes to 30 minutes. As a result, an epoxy resin compound of Example 4 was obtained.

Example 5

4.6 wt % of bisphenol A type epoxy resin, 6.1 wt % of a crystalline epoxy resin represented by Chemical Formula 3, 1.5 wt % of epoxy resin NC-3000, 1.2 wt % of a biphenol hardening agent, 0.1 wt % of 2-methyl imidazole hardening accelerator, and 1 wt % of BYK-W980 additive were all mixed together and then stirred at 40° C. for 10 minutes. Then, 85.5 wt % of an alumina inorganic filler was added thereto, and then the resulting mixture was stirred at room temperature for 20 minutes to 30 minutes. As a result, an epoxy resin compound of Example 5 was obtained.

Comparative Examples

Comparative Example 1

17.1 wt % of bisphenol A type epoxy resin, 2.7 wt % of bisphenol F type epoxy resin, 2.7 wt % of o-cresol-novolac epoxy resin, 5.5 wt % of an epoxy resin NC-3000, 2.1 wt % of a phenol novolac hardening agent, 0.7 wt % of 2-methyl imidazole hardening accelerator, and 0.7 wt % of BYK-W980 additive were all mixed together and then stirred at 40° C. for 10 minutes. Then, 68.5 wt % of an alumina inorganic filler was added thereto, and then the resulting mixture was stirred at room temperature for 20 minutes to 30 minutes. As a result, an epoxy resin compound of Comparative Example 1 was obtained.

Comparative Example 2

11.8 wt % of bisphenol A type epoxy resin, 3.5 wt % of bisphenol F type epoxy resin, 3.5 wt % of o-cresol-novolac epoxy resin, 7.1 wt % of an epoxy resin NC-3000, 2.5 wt % of a phenol novolac hardening agent, 0.5 wt % of 2-methyl imidazole hardening accelerator, and 0.6 wt % of BYK-W980 additive were all mixed together and then stirred at 40° C. for 10 minutes. Then, 70.6 wt % of an alumina inorganic filler was added thereto, and then the resulting mixture was stirred at room temperature for 20 minutes to 30 minutes. As a result, an epoxy resin compound of Comparative Example 2 was obtained.

Comparative Example 3

10.7 wt % of bisphenol A type epoxy resin, 1.8 wt % of bisphenol F type epoxy resin, 1.8 wt % of o-cresol-novolac epoxy resin, 3.6 wt % of an epoxy resin NC-3000, 1.3 wt % of a phenol novolac hardening agent, 0.4 wt % of 2-methyl imidazole hardening accelerator, and 0.4 wt % of BYK-W980 additive were all mixed together and then stirred at 40° C. for 10 minutes. Then, 80.0 wt % of an alumina inorganic filler was added thereto, and then the resulting mixture was stirred at room temperature for 20 minutes to 30 minutes. As a result, an epoxy resin compound of Comparative Example 3 was obtained.

Experimental Example

Measurement of Thermal Conductivity

Thermal conductivities were measured from each Example and Comparative Example by means of a transient hot-wire method by a thermal conductivity meter LFA447 manufactured by NETZSCH as listed in Table 1.

Glass Transition Temperature

Glass transition temperatures were measured at a heating rate of 10° C./min by a differential scanning calorimeter DSC Q100 manufactured by TA Instruments as listed in Table 1.

TABLE 1

| Experiment No. | Thermal Conductivity (W/m · K) | Glass Transition Temperature Tg (° C.) |
|---|---|---|
| Example 1 | 1.99 | 134 |
| Example 2 | 2.24 | 132 |
| Example 3 | 5.13 | 139 |
| Example 4 | 6.32 | 142 |
| Example 5 | 5.28 | 137 |
| Comparative Example 1 | 0.63 | 104 |
| Comparative Example 2 | 1.52 | 115 |
| Comparative Example 3 | 2.865 | 124.78 |

As listed in Table 1, it can be seen that the epoxy resin compounds (Examples 3 to 5) including the epoxy resin represented by Chemical Formula 3 have higher thermal conductivities and glass transition temperatures than those of the epoxy resin compounds (Comparative Examples 1 to 3) without the epoxy resin represented by Chemical Formula 3. Particularly, in comparison of the thermal conductivities between Example 4 and Comparative Example 3 with the same amount of inorganic filler, it can be seen that the thermal conductivity of Example 4 is higher two or more times than that of Comparative Example 3.

Further, if a content of the epoxy resin represented by Chemical Formula 3 is low (i.e. 12 wt % or less) with respect to the whole epoxy resin like Example 1, thermal conductivity is not higher than those of Comparative Examples 1 to 3 but a glass transition temperature is higher as about 130° C.

In accordance with an exemplary embodiment of the present invention, it is possible to obtain an epoxy resin having a mesogen structure that increases crystallinity. Further, it is possible to obtain an epoxy resin compound including the epoxy resin. An insulating layer of high thermal conductivity can be obtained by using the epoxy resin compound and radiant heat performance of a circuit board can be increased.

Since the epoxy resin compound has low absorptivity, low thermal expansibility, and high heat resistance, the epoxy resin compound may be used as an insulating material for various electronic devices.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. An epoxy resin compound comprising:
   an epoxy resin;
   a hardening agent; and
   an inorganic filler,
   wherein the epoxy resin comprises an epoxy resin represented by the following Chemical Formula 1:

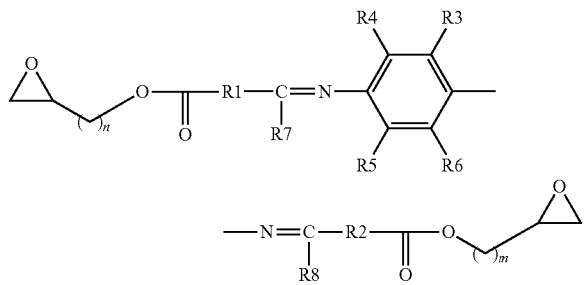

[Chemical Formula 1]

wherein n is from 1 to 3, m is from 1 to 3, $R^1$ represents one to three aryl groups, $R^2$ represents one to three aryl groups, and $R^3$, $R^4$, $R^5$, $R^6$, $R^7$ and $R^8$ are independently selected from the group consisting of hydrogen, an alkyl group having 1 to 30 carbon atoms, a halogen, an aryl group, an alkoxy group, an amino group, a hetero aryl group, and a carboxylic group, and
wherein at least one of $R^7$ and $R^8$ is a halogen.

2. The epoxy resin compound of claim 1, wherein the epoxy resin is an epoxy resin represented by the following Chemical Formula 2:

[Chemical Formula 2]

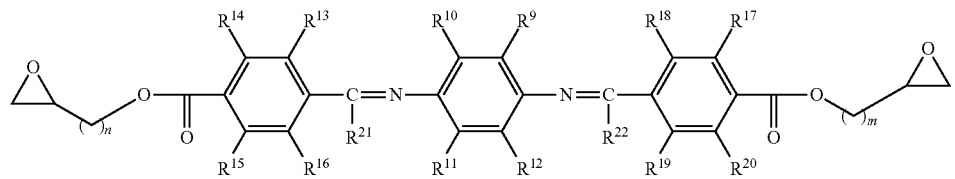

wherein n is from 1 to 3, m is from 1 to 3, and $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently selected from the group consisting of hydrogen, an alkyl group having 1 to 30 carbon atoms, a halogen, an aryl group, an alkoxy group, an amino group, a hetero aryl group, and a carboxylic group, and wherein at least one of $R^{21}$ and $R^{22}$ is a halogen.

3. The epoxy resin compound of claim 1, wherein the inorganic filler is included in 40 wt % to 97 wt % with respect to a total weight of the epoxy resin compound.

4. The epoxy resin compound of claim 1, wherein the inorganic filler includes at least one of alumina, boron nitride, aluminum nitride, crystalline silica and silicon nitride.

5. The epoxy resin compound of claim 1, wherein the epoxy resin is included in 3 wt % to 60 wt % with respect to a total weight of the epoxy resin compound.

6. The epoxy resin compound of claim 1, wherein the epoxy resin further comprises at least one non-crystalline epoxy resin.

7. The epoxy resin compound of claim 1, wherein the epoxy resin is an epoxy resin represented by the following Chemical Formula 4:

group having 1 to 30 carbon atoms, a halogen, an aryl group, an alkoxy group, an amino group, a hetero aryl group, and a carboxylic group, and wherein at least one of $R^{23}$ and $R^{24}$ is a halogen.

8. The epoxy resin compound of claim 1, wherein the epoxy resin represented by Chemical Formula 1 is included in 12 wt % or more with respect to the whole epoxy resin.

9. A radiant heat circuit board comprising:
a metal plate;
an insulating layer formed on the metal plate; and
a circuit pattern formed on the insulating layer,
wherein the insulating layer is formed by hardening the epoxy resin compound of claim 1.

10. The radiant heat circuit board of claim 9, wherein the inorganic filler is included in 40 wt % to 97 wt % with respect to a total weight of the epoxy resin compound.

11. The radiant heat circuit board of claim 10, wherein the inorganic filler includes at least one of alumina, boron nitride, aluminum nitride, crystalline silica and silicon nitride.

12. The radiant heat circuit board of claim 11, wherein the epoxy resin represented by Chemical Formula 1 is included in 12 wt % or more with respect to the whole epoxy resin.

13. The epoxy resin compound of claim 1, wherein, among $R^3$, $R^4$, $R^5$, and $R^6$, at least one is different from the others.

[Chemical Formula 4]

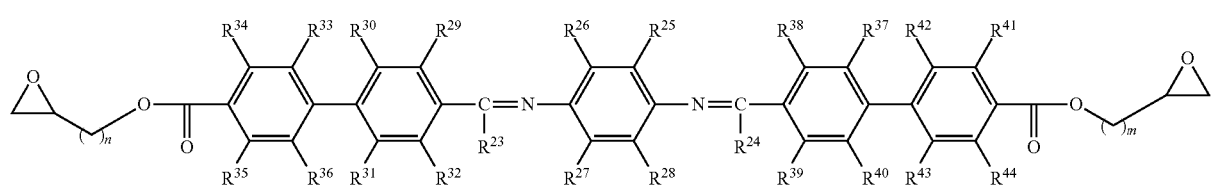

wherein n is from 1 to 3, m is from 1 to 3, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, and $R^{44}$ are independently selected from the group consisting of hydrogen, an alkyl 14. The epoxy resin compound of claim 1, wherein $R^7$ is a halogen and $R^8$ is a halogen.

15. An epoxy resin represented by the following Chemical Formula 1:

[Chemical Formula 1]

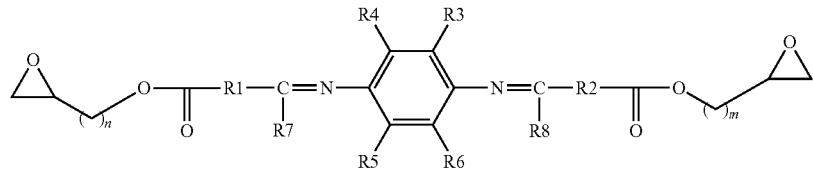

wherein n is from 1 to 3, m is from 1 to 3, $R^1$ represents one to three aryl groups, $R^2$ represents one to three aryl groups, and $R^3$, $R^4$, $R^5$, $R^6$, $R^7$ and $R^8$ are independently selected from the group consisting of hydrogen, an alkyl group having 1 to 30 carbon atoms, a halogen, an aryl group, an alkoxy group, an amino group, a hetero aryl group, and a carboxylic group, and wherein at least one of $R^7$ and $R^8$ is a halogen.

16. The epoxy resin of claim 15, wherein, among $R^3$, $R^4$, $R^5$, and $R^6$, at least one is different from the others.

* * * * *